United States Patent [19]
Bosniak et al.

[11] Patent Number: 5,169,384
[45] Date of Patent: Dec. 8, 1992

[54] APPARATUS FOR FACILITATING POST-TRAUMATIC, POST-SURGICAL, AND/OR POST-INFLAMMATORY HEALING OF TISSUE

[76] Inventors: Stephen L. Bosniak, 12 Gay St., New York, N.Y. 10014; Paul T. Kolen, 7212 Linden Ter., Carlsbad, Calif. 92009

[21] Appl. No.: 746,658

[22] Filed: Aug. 16, 1991

[51] Int. Cl.⁵ .......................... A61N 1/30; A61N 1/28; A61F 7/02
[52] U.S. Cl. ..................... 604/20; 128/399; 128/783; 128/793; 128/798; 128/802
[58] Field of Search .................. 604/20; 128/399, 783, 128/793, 798, 802

[56] References Cited

U.S. PATENT DOCUMENTS

| | | |
|---|---|---|
| 887,482 | 5/1908 | Lammers et al. |
| 1,626,617 | 5/1927 | Last . |
| 1,692,669 | 11/1928 | Last . |
| 1,715,027 | 5/1929 | Benjamin . |
| 1,786,541 | 12/1930 | Last . |
| 2,078,391 | 4/1937 | Last . |
| 2,635,175 | 4/1953 | Hodge . |
| 3,447,537 | 6/1969 | King . |
| 3,971,387 | 7/1976 | Mantell . |
| 4,116,238 | 9/1978 | Pettijohn . |
| 4,141,359 | 2/1979 | Jacobsen et al. . |
| 4,317,457 | 3/1982 | Guillot ............................ 128/783 |
| 4,556,051 | 12/1985 | Maurer ...................... 128/798 X |
| 4,585,002 | 4/1986 | Kissin .............................. 128/399 |
| 4,689,039 | 8/1987 | Masaki ............................ 604/20 |
| 4,752,285 | 6/1988 | Petelenz et al. ................ 604/20 |
| 4,764,164 | 8/1988 | Sasaki ............................... 604/20 |
| 4,842,577 | 6/1989 | Konno et al. ................... 604/20 |
| 4,860,748 | 8/1989 | Chiurco et al. .............. 128/399 |
| 4,931,046 | 6/1990 | Newman .......................... 604/20 |
| 4,944,044 | 7/1990 | Zarotti . |
| 4,950,229 | 8/1990 | Sage, Jr. ......................... 604/120 |
| 4,979,938 | 12/1990 | Stephen et al. ................ 604/20 |
| 5,038,797 | 8/1991 | Batters .......................... 128/798 |
| 5,053,001 | 10/1991 | Reller et al. .................... 604/20 |

FOREIGN PATENT DOCUMENTS

| | | | |
|---|---|---|---|
| 330742 | 8/1989 | European Pat. Off. ............ | 128/399 |
| 8808729 | 11/1988 | PCT Int'l Appl. ................ | 128/803 |
| 8905129 | 6/1989 | PCT Int'l Appl. ................ | 128/399 |
| 502167 | 3/1939 | United Kingdom . | |

Primary Examiner—Randall L. Green
Assistant Examiner—Mary Beth O. Jones
Attorney, Agent, or Firm—Venable, Baetjer & Howard

[57] ABSTRACT

A temperature variable and iontophoretic device for application to the body of a patient has an outer support member coupled to a device for selectively applying thermal energy to the body of a patient or for removing thermal energy therefrom, and a further device for selectively energizing the thermal energy supply and removal device. Another member is coupled to the outer support member for iontophoretically administering a compound to the body of the patient. The energizing device comprises a user-operable data input device which also controls the iontophoretic administering device. Transcutaneous electrical neurostimulation (TENS) can also be provided.

26 Claims, 7 Drawing Sheets

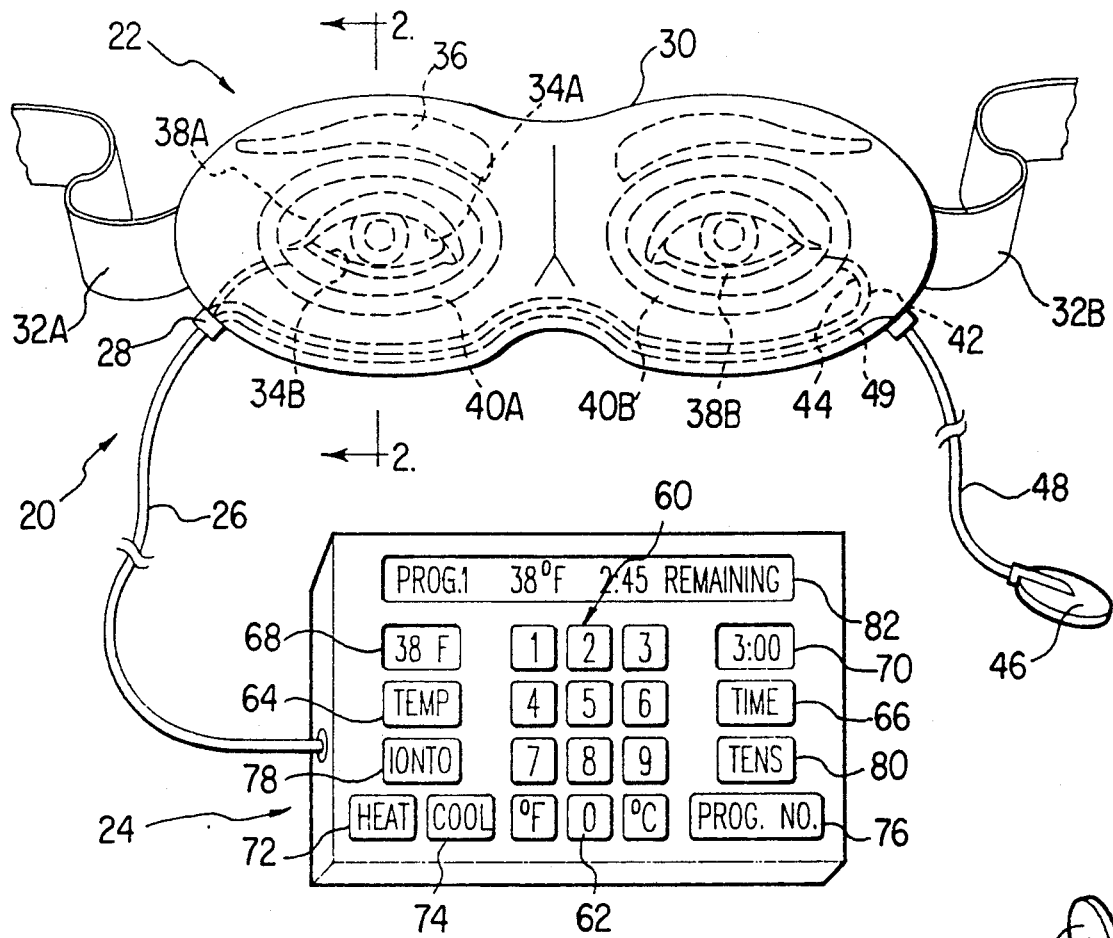
FIG. 1
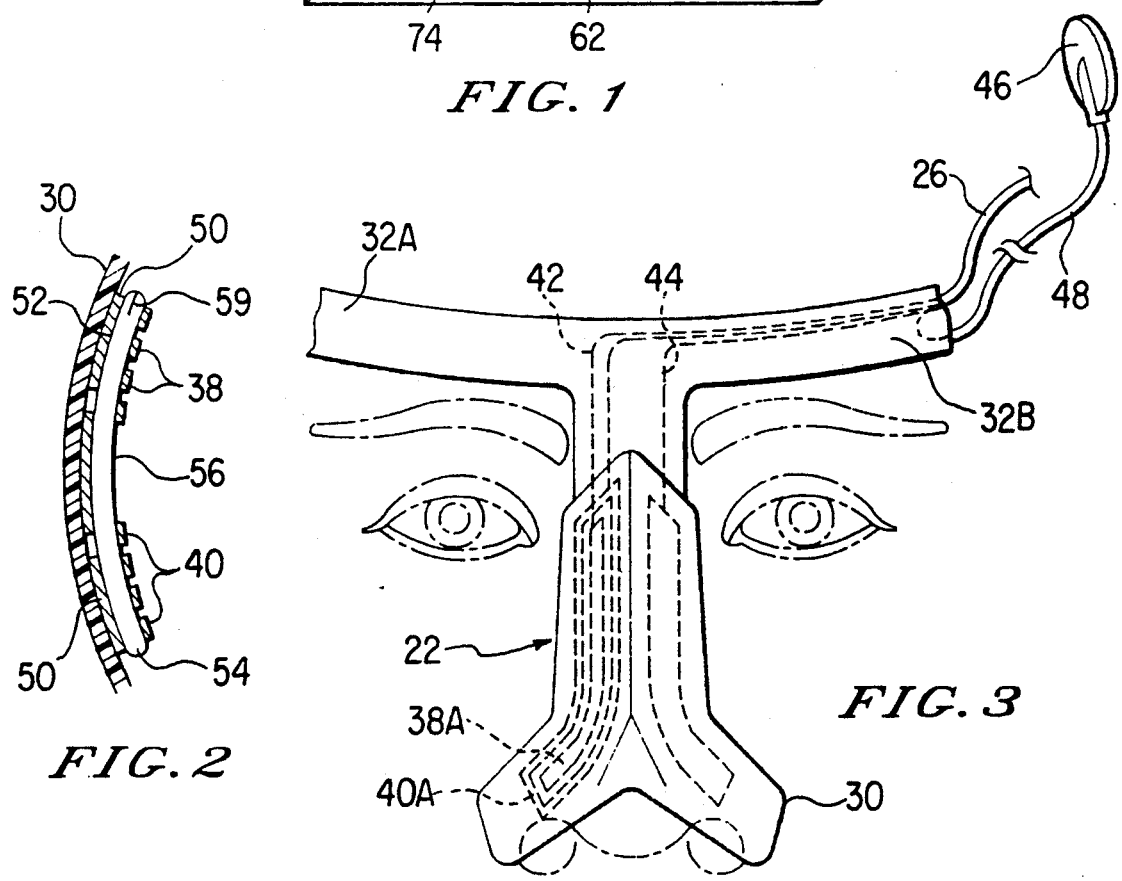
FIG. 2
FIG. 3

APPARATUS FOR FACILITATING POST-TRAUMATIC, POST-SURGICAL, AND/OR POST-INFLAMMATORY HEALING OF TISSUE

BACKGROUND OF THE INVENTION

1. Field of the Invention

The invention relates generally to method and apparatus for providing therapeutic applications, and more particularly to therapeutic applications for reducing swelling, treating skin and/or tissue, and for facilitating tissue healing as a result of trauma resulting from, for example, surgery, forceful impacts, strains and sprains, or any other inflammatory or allergic reactions.

2. Description of the Related Art

Post-surgical trauma and trauma resulting from, for example, sports-related injuries, is a common occurrence with which patients must regularly contend. The trauma oftentimes manifests itself in the form of swelling which results from the accumulation of bodily fluids underlying the skin adjacent to the site of the trauma. Such swelling not only results in patient discomfort, but also inhibits recovery, as it results in an increased application of pressure against the tissue and surrounding nerve and organ structures. Furthermore, such swelling reduces patient mobility when the trauma is of an orthopedic nature. For all of the foregoing reasons, it is a common objective of health care professionals to reduce the accumulation of undesired fluid underlying the site of patient trauma as soon as possible. To date, such fluid reducing measures have typically encompassed the application of cold compresses such as ice packs for prescribed periods of time to the site of the trauma, followed by the application of hot compresses.

Prior to the development of the present invention, these known therapeutic processes have met with only limited success, as the cold compresses are oftentimes initially too cold for the patient to comfortably tolerate and, as a result, the patient is unable to tolerate the cooling effects of the compresses for the prescribed period of time. Furthermore, because the compresses remove heat from the body, the temperature of the compresses themselves progressively increases, thereby diminishing their temperature reducing affects. Longer periods of cooling can be provided by increasing the amount of coolant such as ice in the cold compress; however, such practices increase the size of the compress, thereby adversely impacting upon the compresses' ability to conform to the site of the trauma and compromising their effectiveness in removing heat from the site of the injury. An optimal regimen for reducing tissue swelling provides for treatment with cold compresses for up to about 72 hours followed by warm compress treatment for a period of about 10-14 days. Furthermore, because water has a high specific gravity, the provision of additional quantities of ice in the cold compress further increases the downward pressure exerted against the trauma site, thereby negating to some extent the benefits afforded by cold compress treatment. Further problems arise as a result of the considerable time demands of personnel at health care facilities, as the cold and hot compresses used in such facilities oftentimes cannot be properly monitored and changed prior to loss of their effectiveness, particularly during overnight and prolonged stays. As a result of all of the foregoing deficiencies in the prior art, patient recovery from physical trauma surgery and inflammation is often prolonged, resulting in increased patient discomfort, lack of motility in instances of orthopedic trauma, and prolonged periods of patient medication resulting from discomfort arising from the trauma and the prolonged presence of subcutaneous swelling.

It is further known in the art that patient recovery from trauma can be expedited by the application of transcutaneous electrical neurostimulation (TENS), which typically involves the application of an alternating current (AC) potential to the tissue by way of two or more electrodes of opposite polarity Patient recovery can further be enhanced in some instances through the application to the skin of ionic and ionizable substances which can be transdermally delivered through the skin. Such transdermal or iontophoretic transport provides for the migration of the ionic substance along electric field lines established by the iontophoretic transport device. However, a limitation of such transdermal transport devices is the orientation of the field along a plane that is generally parallel to the surface of the skin, resulting in migration of the ionizable substance along the skin rather than transversely through the skin.

In view of the foregoing, it would be desirable to provide for the processes of compress treatment, transcutaneous electrical neurostimulation and iontophoretic transport through the skin of ionic compounds without the above-noted deficiencies. It would further be advantageous to provide apparatus and methods which combine any one or more of the foregoing processes in order that they may be substantially simultaneously applied to the patient. It would further be advantageous to provide such apparatus and methods which provide for automatic administration and termination of such treatment processes after a user-selected time interval has passed. These and other objectives have provided the motivation for development of invention described herein.

BRIEF DESCRIPTION OF THE DRAWINGS

FIG. 1 is a front view of one embodiment of the invention for treatment of the upper facial portion of a patient;

FIG. 2 is a sectional view along the line 2—2 of FIG. 1;

FIG. 3 is a front view of the applicator portion of another embodiment of the invention which has particular applicability in post-nasal reconstructive surgical procedures;

SUMMARY OF THE INVENTION

Figure 4:
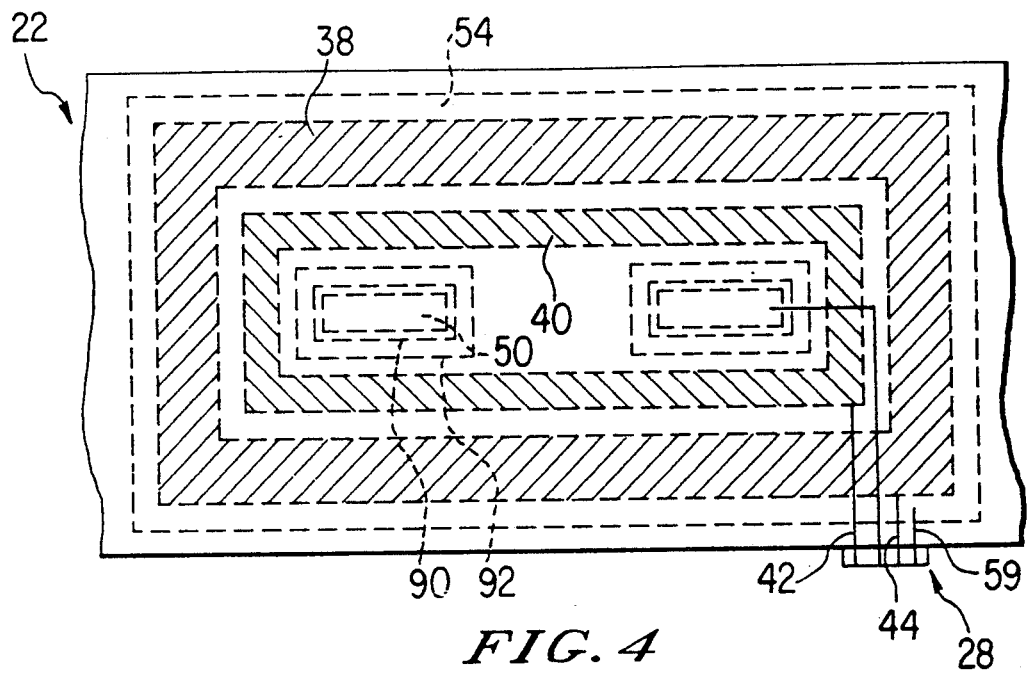
FIG. 4 is a rear elevational view of a further embodiment of the invention.

Various apparatus and methods are disclosed which provide for facilitation of patient recovery from post-traumatic, post-surgical, and/or post-inflammatory tissue conditions. The disclosed apparatus and methods provide for various combination of thermal therapy (hot/cold), transdermal ionic compound delivery, and transcutaneous electrical neurostimulation (TENS) and are particularly advantageous for use in instances where it is desirable to provide for time treatment for prolonged periods of time, as can occur, for example, during patient recovery from various surgical procedures and from prolonged immobilization by orthopaedic appliances such as casts, as prescribed treatment regimes can be implemented in accordance with such user-selected parameters as duration of time and operations temperature. Treatment can be accomplished by fabricating a device which provides for any one or more of the foregoing tissue treatment processes as an implantable or non-implantable device with respect to the body of a patient, and is implementable in conventional and micro-gravity environments.

DETAILED DESCRIPTION OF THE PREFERRED EMBODIMENTS

With reference to the drawings, wherein like reference characters represent corresponding parts throughout the various views, and with particular reference to FIG. 1, there is depicted a tissue treatment device in accordance with the subject invention, designated generally by reference character 20. The treatment device 20 generally comprises a therapeutic applicator device or mask 22 and a system controller/input device 24 that is connected to the applicator 22 by an electrical cord 26. Preferably, the cord 26 is connected at one end thereof to the applicator device 22 by way of a detachable coupling 28. The exterior 30 of the applicator device 22 is configured as a semi-rigid support member which is securable to the upper facial portion of a patient by an adjustably-positionable strap 32. The strap 32 can be in a form of an elasticized strap or a pair of mutually engageable strap elements 32A and 32B, each of which is provided with complementary components of a hook-and-loop fastener of the type sold under the trademark VELCRO. While the mask 22 can be configured and dimensioned in accordance with the site of treatment and the nature of the underlying tissue, the depicted mask is of a type which is especially adapted for use in facilitating patient recovery from surgical reconstruction of the eyelids. Accordingly, the mask is dimensioned so as to extend over the upper and lower eyelids, illustrated in phantom by lines 34A and 34B, and eyebrows 36. Overlying the eyelids 34A and 34B of each eye is a concentric array of electrodes 38A and 38B and 40A and 40B. The innermost electrode 38 overlying each eye provides for transcutaneous electrical neurostimulation (TENS) of the tissue in the vicinity of electrode. The outer electrode 40 provides for iontophoretic or transdermal application of ionic or ionizable compounds. Suitable compounds for iontophoretic transport include medicinal compounds such as steroids and antibiotics, as well as lubricating and/or moisturizing creams and other topical treatments. The respective TENS and iontophoresis electrodes are electrically connected to the input device 24 by way of electrical connector leads 42 and 44, respectively, which communicate with the connector cord 26 in a conventional manner. A third electrode 46 preferably extends from the applicator device 22 along a connector lead 48 which is of a sufficient length to permit securing of the electrode 46 to a back portion of the neck of the patient. The third electrode 46 is particularly useful in establishing an iontophoresis electric field which extends generally transverse to the plane of the skin surface under treatment, thereby facilitating iontophoretic transport of the ionizable compound through the skin. Orientation of the iontophoresis electric field in this manner is preferable to that provided in conventional iontophoresis transport devices, as such typically provide for the generation of electric fields which extend generally parallel rather than transverse to the plane of the tissue surface. Accordingly, transmittance through the skin of the desired ionic compounds is inhibited in these known devices because the ionic compounds tend to follow the plane of the generated electric field. Details of operations of the TENS electrodes 38 and iontophoresis electrodes 40 and 46 will be described in greater detail below.

With reference to FIGS. 1 and 2, further details of the tissue treatment device of the subject invention will be described. In addition to the above-mentioned TENS and iontophoretic capabilities, the applicator device 22 preferably further includes suitable means such as Peltier thermoelectric transfer devices 50 that are interposed between the inner surface of the mask outer layer 30 and the outer surface 52 of a fluid filled deformable member 54. The deformable member 54 is configured as a fluid impervious membrane which extends substantially along the interior surface of the mask 22. The deformable member 54 is filled with a fluid such as an alcohol/water mixture having a relatively low specific gravity and relatively high heat capacity. The TENS and iontophoresis electrodes 38 and 40 are positioned along the interior surface 56 of the deformable member so as to be positioned in close proximity and preferably in physical engagement with the underlying skin surface upon application of the device 22 to the tissue site to be treated. While a single Peltier device 50 of suitable current handling (and therefore thermal energy exchanging) capacity can be provided, in the preferred embodiment of the invention several Peltier devices are provided in spaced relationship, as shown as FIG. 2, in order to facilitate molding of the deformable member 54 to the contour of the underlying skin surface. For the same reason, the TENS and iontophoresis electrodes 38 and 40 are configured as relatively thin, electrically conductive members which are preferably secured to the deformable member interior surface 56 in a suitable manner, such as by way of electrodeposition.

Appropriate signal control input is provided to the respective TENS and iontophoresis electrodes 38 and 40, and Peltier devices 50 by way of the controller/input device 24 (FIG. 1). The controller 24 incorporates all of the necessary electrical power and components that are associated with operation of the device 22. The electrical circuitry will be described in greater detail below, particularly with reference to FIGS. 4-8. As in shown FIG. 1, the controller 24 includes a digital key pad, denoted generally by reference character 60, that is comprised of a plurality of alphanumeric keys 62, independently actuable selectors switches 64 and 66 for temperature and time, respectively, and displays 68 and 70 for the respective temperature and time selection parameters that are selected by actuation of the appropriate selector switches 64, 66 and alpha-numeric keys 62. The device 24 further includes independent heating and cooling parameter switches 72 and 74, respectively, and a program number selector 76 for entering into the system data relating to the establishment of one or more system programs for treatment of the tissue or skin underlying the mask 22 in the manner described below. Separate selector switches 78 and 80 are provided for selection of iontophoresis and transcutaneous electrical neurostimulation (TENS). A display 82 is provided along the upper portion of the device for displaying, for example, data relating to the particular treatment program in progress. Such program related data could include, for example, the program number, the temperature of the fluid within the deformable member 54, and the time remaining for a given program. In addition, suitable indicia can be provided to indicate the enablement status of the iontophoresis and TENS selector switches. It is to be appreciated that any one or all of the heating/cooling, iontophoresis, and transcutaneous electrical neurostimulation functions can be selected in accordance with such factors as the nature of the treatment to be provided, the site of treatment along the body of the patient, and user preference. It is to be further appreciated that any one or more of the foregoing functional capabilities can be selectively included or omitted from the tissue treatment device 20 in accordance with the foregoing factors.

FIG. 3 illustrates an alternative embodiment of the tissue treatment device 20 depicted in FIG. 1 and described above, in which the therapeutic applicator or mask portion 22 thereof is configured so as to overlie the nose of a patient. As with the mask 22 of the device depicted in FIG. 1, the mask 22 of the device depicted in FIG. 3 is generally bilaterally symmetrical with respect to its longitudinal axis. The exterior 30 of the mask is configured as a generally rigid, flexible member of the type which can be readily fabricated from a suitable thermoplastic material. The illustrated mask 22 can include all of the capabilities of the mask depicted in FIG. 1 as, for example, by positioning TENS and iontophoresis electrodes 38 and 40A and 40B the interior surface of the rigid support 30 so as to be positioned adjacent to the tissue of the nose. The fluid filled deformable member 54 (FIG. 2) can optionally be provided intermediate the electrodes 38 and 40 and support 30 to provide for cushioning as well as thermal exchange when Peltier devices 50 are provided. In instances where iontophoresis treatment is desired, the third electrode 46 can be provided. As noted previously, this third iontophoresis electrode allows the user to vary the directional orientation of the electric field extending between the electrodes 4 and 46 so as to enhance iontophoretic medication delivery.

Figure 5:
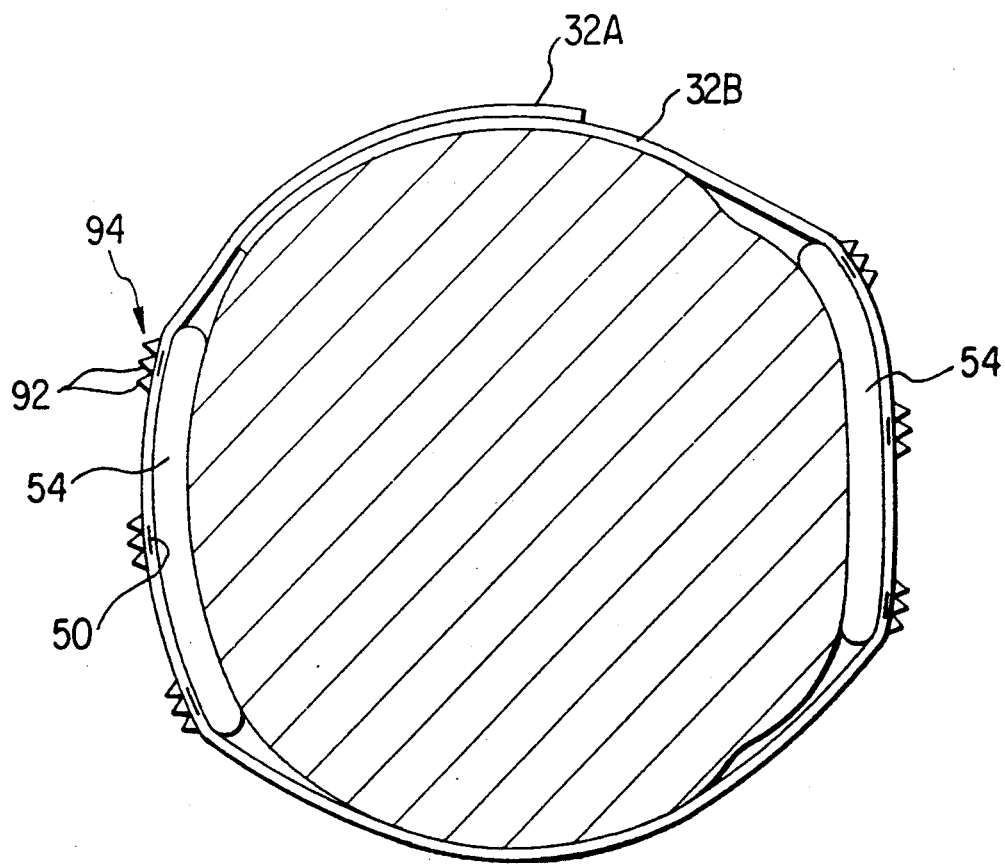
FIG. 5 illustrates use of the apparatus depicted in FIG. 4 on the body of a patient.

A further alternative embodiment of the tissue treatment device of the present invention is provided in FIGS. 4 and 5, in which the therapeutic applicator device 22 is configured as an elongated, generally flexible and adjustably tensionable member. The outer support 30 of the device is formed from a flexible, tensionable material such as neoprene rubber which includes the array of TENS and iontophoresis electrodes 38 and 40, respectively, that are positioned along an inner, tissue-facing surface of a deformable, fluid filled member 54. The one or more Peltier heating/cooling devices 50 are interposed between the outer surface of the deformable member 54 and the inner surface of the applicator support 30. An aperture 90 extends through the support member 30 to permit thermal communication between the Peltier devices 50 and a corresponding heat sink 92. The heat sink 92 is formed from a suitable lightweight, heat conductive metal such as aluminum and is provided with a corrugated or ribbed exterior configuration as indicated by reference numeral 94, so as to maximize the available surfaced area by which heat can be radiated from the heat sink 92 into the surrounding atmosphere.

The elongated applicator device 22 can be provided with one or more sets of TENS and iontophoresis electrodes 38 and 40 and heat exchange devices such as Peltier devices 50 along its length. In the device depicted in FIG. 5, two such units are provided so as to be generally opposed from one another along the periphery of a structure such as the knee of a patient. The applicator device 22 is adjustably tensionable by engaging mutually engagable hook and loop members provided along straps 32A and 32B in the manner described above to provide a user-selected level of tension to the anatomical structure to be treated. A controller and data input device (not shown) of the type designated by reference character 24 (FIG. 1) can be provided to allow selection of the desired tissue treatment parameters described above. In all of the foregoing embodiments of the invention, a length of connector cord 26 is provided between the controller 24 and applicator device 22 to permit mounting of the controller, for example, to the waist of the patient or adjacent to a neighboring support structure. This facilitates both accessibility and visibility of the controller so that the progress of the various programs to be implemented thereby can be easily monitored and controlled.

Figure 6:
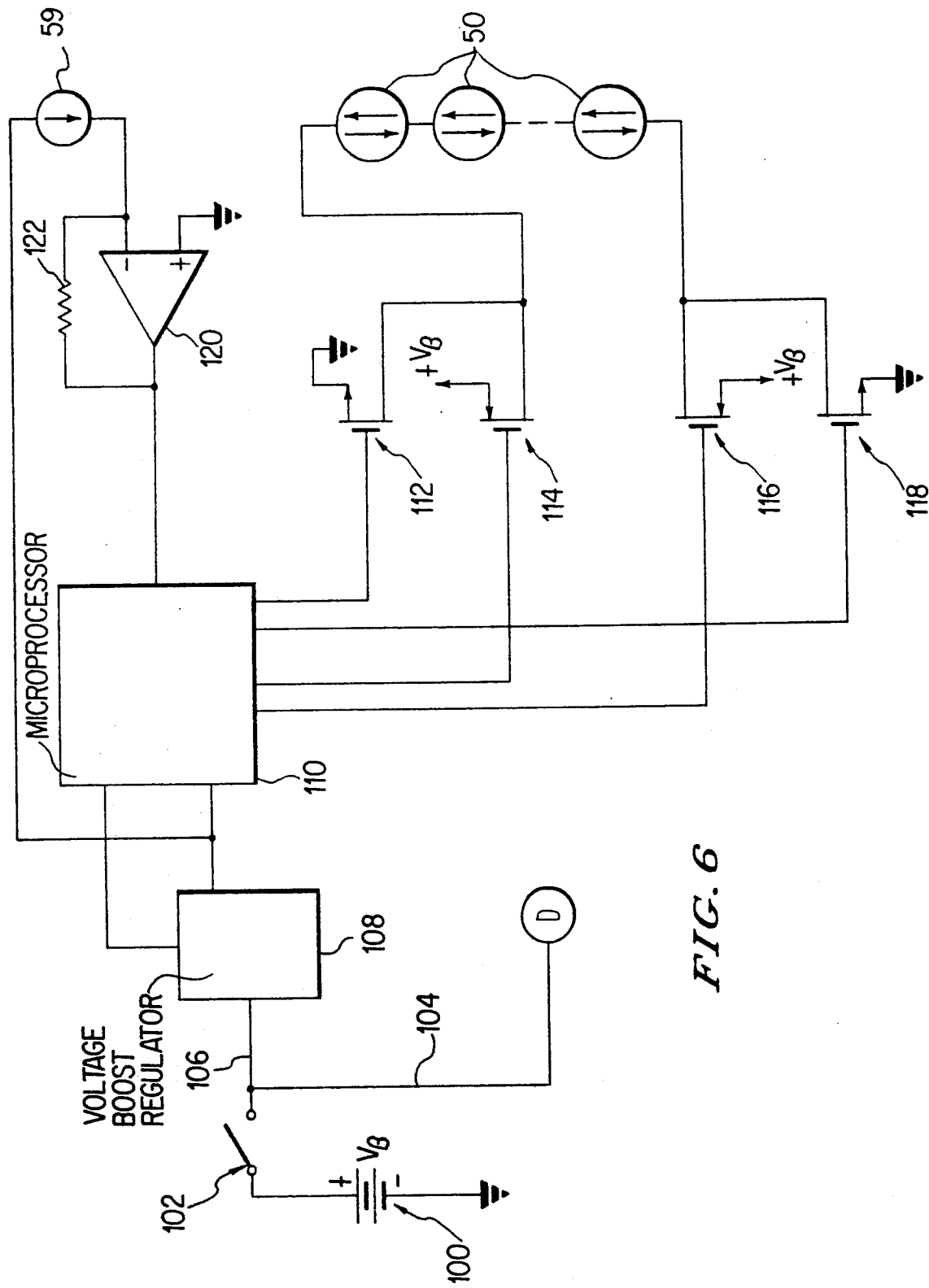
FIG. 6 is a schematic illustration of the electrical circuitry for providing electrical stimulation in accordance with one embodiment of the invention.
Figure 7:
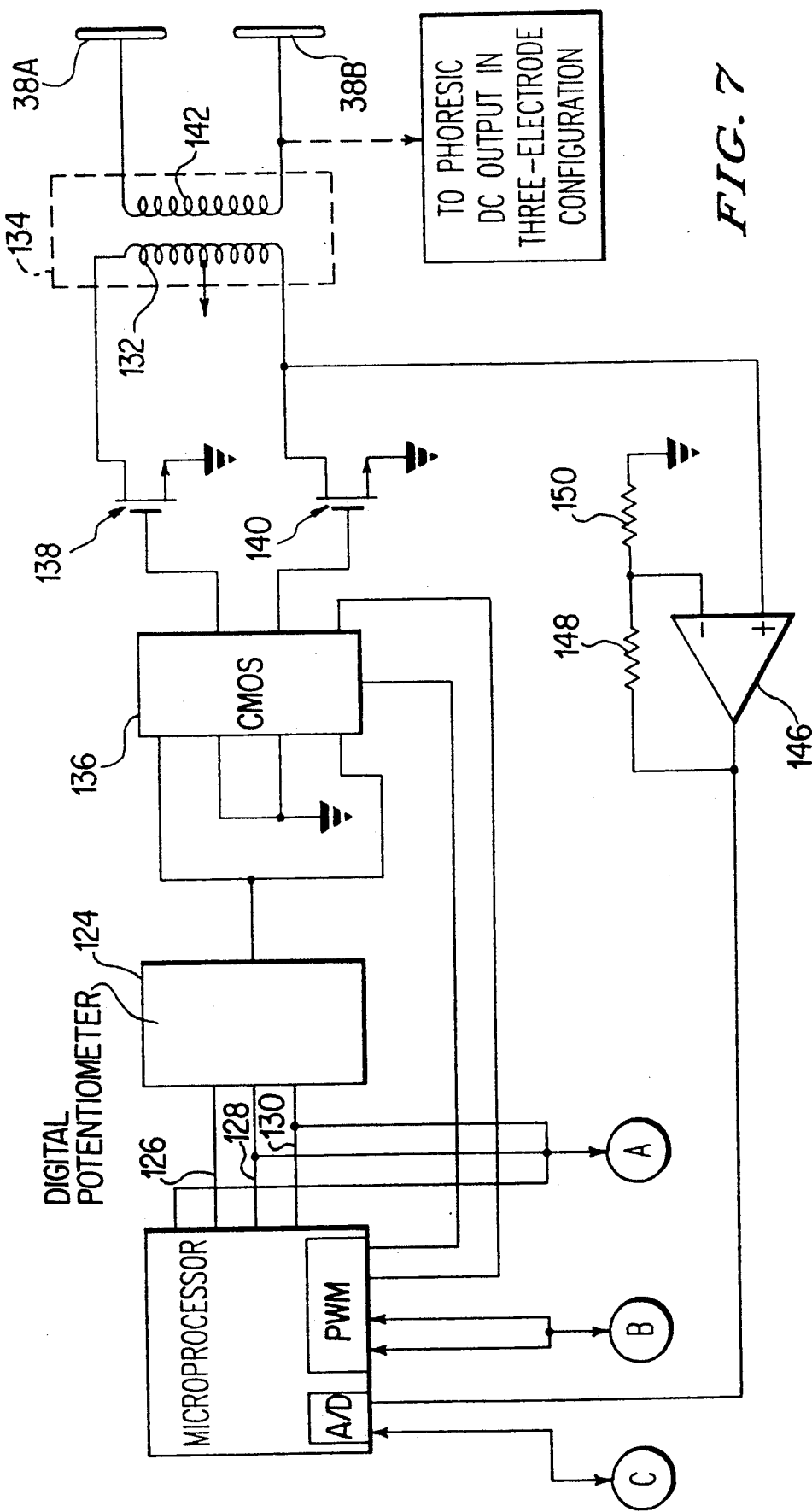
FIG. 7 is schematic illustration of the electrical circuitry for providing electrical stimulation in accordance with another embodiment of the invention.
Figure 8:
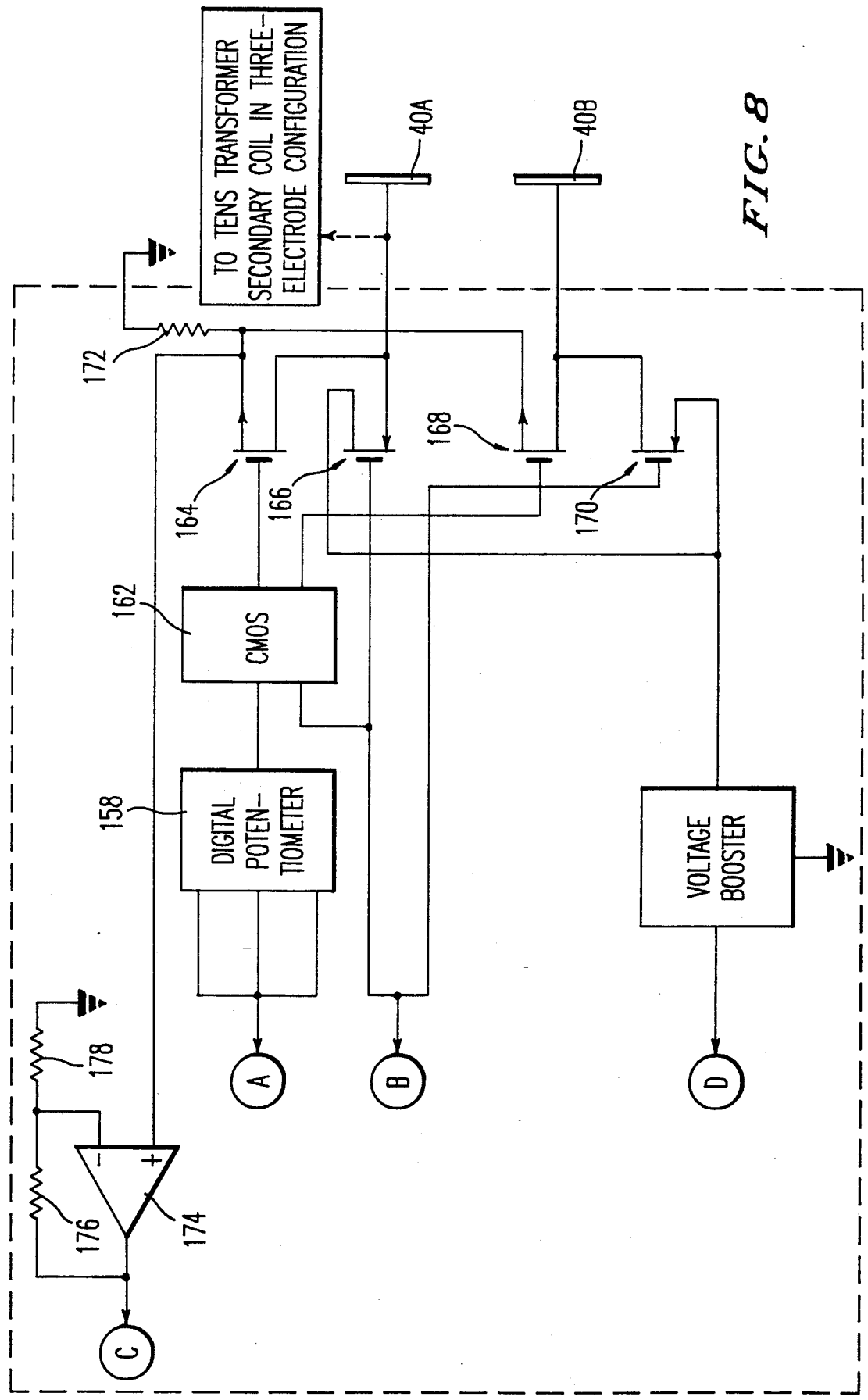
FIG. 8 is a schematic illustration of the electrical circuitry for providing electrical stimulation in accordance with a further embodiment of the invention.

With reference to FIGS. 6-8, there are depicted electrical schematic diagrams of control circuits for the Peltier heat exchanger, transcutaneous electrical neurostimulation electrodes, and iontophoresis electrodes, respectively. With reference to FIG. 6, a suitable power source 100 such as a DC battery pack provides power to the circuit components through a switch 102. Auxiliary power can be provided along line 104 to both power the circuit and to recharge the DC power source 100. Electric current passing along line 106 from the respective power supply passes through a voltage regulator 108 which provides a steady 5-volt supply for the downstream electronics. Output from the voltage regulator 108 is directed to a suitable processor unit 110 such as a Motorola Model 68HC11. Use of the 6SHC11 processor is advantageous, as it provides not only a processor, also 256 bytes of RAM, 12K of EPROM for the application program, 512 bytes of EEPROM for receiving variable program input, a serial interface port for coupling with external processing and input devices, interrupts, and an 8-channel multiplex A/D converter. Software stored in RAM terminates the supply of power to the voltage regulator 108 in instances where voltage below a prescribed minimum appears at the output of the regulator 108. A plurality of pulse-width modulated drivers 112, 114, 116, and 118 is provided for control of the heating and cooling functions of the tissue treatment device 20. Drivers 114 and 116 are dedicated for heating and cooling selection, respectively, and each is paired with a corresponding driver 112 and 118, respectively. Output from the respective driver pairs 112, 114 and 116, 118 is directed to the respective Peltier heat exchange devices 50 for implementing an exchange of thermal energy with the heat exchange medium carried within the deformable member 54. Heat exchange through the fluid within the deformable member 54 is preferred over heat exchange directly with the skin of the patient so as to provide for more even distribution of thermal energy across the surface of the skin of the patient under treatment. As is well known in the electronics art, Peltier heat exchange devices are operable to radiate or to receive heat in accordance with the direction of current flow through the device. However, versatility is afforded at the cost of inefficiency. Accordingly, signal input to the heat exchange devices 50 is pulse-width modulated so as to minimize power drained from the DC power source 100. Temperature control signal input to the heat exchange devices 50 is pulse-width modulated by the appropriate one of the drivers 112 and 118 in accordance with the particular heating or cooling function that has been selected. The temperature of the fluid medium within the deformable member 54 is sensed by the temperature probe 59 (FIG. 1), which is preferably in the form of a thermoelectric sensor such as the Analog Devices Model AD 590. This particular sensor which provides an output of 1 microamp per °K. of sensed temperature. Current output from the thermosensor 59 is converted to an appropriate voltage by the current-to-voltage converter 120 and associated resistor 122. In accordance with the voltage drop between the processing unit 110 and the converter 120, signal output is directed to the respective one of the drivers 112 and 118 so as to modify the current to the Peltier heat exchangers 50. In this way, the Peltier devices can be made to supply thermal energy to, or remove thermal energy from, the fluid within the deformable member 54.

With reference to FIG. 7, details are shown of the circuitry which is used to control the transcutaneous electrical neurostimulation function that is afforded by the treatment device of the present invention. Such treatment is particularly beneficial to stimulate muscle response during prolonged periods of relative inactivity as can occur, for example, during prolonged periods of immobilization in orthopaedic appliances such as casts and exposure to micro-gravitational environments. Power is supplied to the microprocessor unit 110 in the manner described above in connection with FIG. 6. The signal output from the microprocessor unit 110 is directed to a digital potentiometer 124 along control lines 126, 128 and 130. Control line 126 provides for chip selection for the potentiometer 124. Control line 128 is an up/down control input line. Control line 130 provides for incrementing of the potentiometer 124. The potentiometer provides a variable gate voltage to the primary coil 132 of the TENS transformer 134 so as to provide for amplitude control of the signal passing through the transformer. Prior to arrival at the transformer primary coil, signal output from the digital potentiometer 124 passes through a digitally controlled CMOS transmission gate 136. A pair of MOSFETs 138 and 140 are driven in a complimentary push-pull fashion in order to generate an AC voltage signal on the secondary coil 142 of the transformer 134. The secondary coil 142 is connected to the respective TENS electrodes 38 to provide electrical stimulation of the tissue in the vicinity of the electrodes. The electric current passing through the transformer primary coil 132 is sensed for feedback control of the induced TENS current provided to the electrodes 38. This feedback control is provided by the current-to-voltage converter 146, which is operable to sense voltage drop across the MOSFET 140. The output signal from the converter 146 is therefore proportional to the TENS output from the transformer primary coil 132 and thus provides for closed loop feedback control to the microprocessor 110 for TENS control. Signal output from the converter 146 is conditioned by series resistors 148 and 150 in a standard op-amp configuration to provide voltage gain to the A/D converter of the microprocessor unit 110 In this way, the voltage supplied to the A/D converter is maintained within the limits of the converter in order to obtain maximum signal resolution.

Details of the iontophoretic drive system are shown in FIG. 8. The driver is indicated generally by reference character 156, and includes a second digital potentiometer 158 to provide for control of the level of phoresic current in accordance with the input lines 128, 130 and 160. Control line 160 is a second chip select line extending between the microprocessor unit 110 (FIGS. 6 and 7) and the potentiometer 158. As is the case with the control lines 126, 128 and 130 (FIG. 7) for the potentiometer 124, three control lines are provided for operation of the potentiometer 158 of the phoresic driver 158. The potentiometers 124 and 158 are multi-step potentiometers such as the Xicor Model X9C 503, which provides for 100 steps of signal control. The control voltage produced by the potentiometer 158 is applied to a second CMOS transmission gate 162, the output of which is applied to the polarity select/amplitude control gates of the MOSFETs 164, 166, 168 and 170. DC power is provided to the iontophoresis electrodes 40 through MOSFETs 166 and 168 for the establishment of an electric field at the tissue site in the vicinity of the electrodes 40. A current sensing resistor 172 extends between the MOSFETs 164 and 168 and provides for closed loop feedback control of the phoresic drive current through a current-to-voltage converter in a fashion similar to that provided by the current-to-voltage converter 146 described above in connection with the TENS circuitry (FIG. 7). Resistors 176 and 178 are provided in a conventional op-amp configuration to provide voltage gain to the A/D converter of the microprocessor unit 110, so that the that voltage supplied to the microprocessor A/D converter is within its operational limits.

Figure 9:
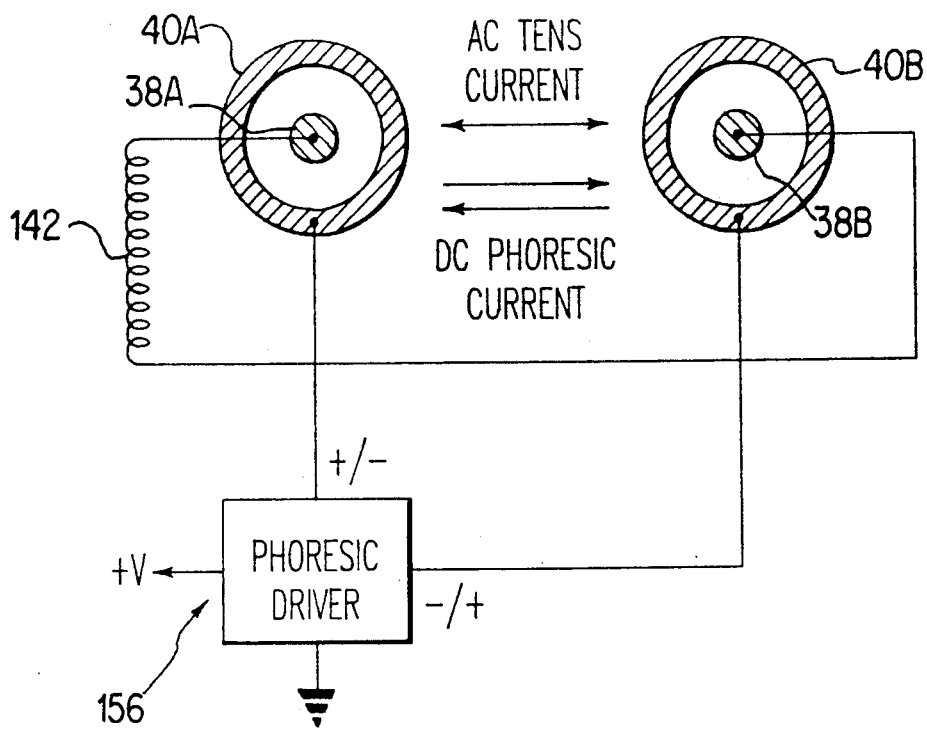
FIG. 9 is a schematic illustration of an electrode configuration for use in the present invention.

As indicated above in connection with the respective embodiments of the tissue treatment device 20 illustrated in FIGS. 1 and 3, the device 20 is operable, for example, in a two-electrode or a three-electrode configuration. With reference to the two-electrode configuration, FIG. 9 diagrammatically illustrates the circuit arrangements provided by FIGS. 7 and 8 for the respective TENS and iontophoresis drivers. With reference to the drawing, the phoresic driver 156 is shown connected to the respective iontophoresis electrodes 40a and 40b in such a fashion as to provide the electrodes with opposite voltage polarity. Accordingly, a DC phoresic current is established between the electrodes 40a and 40b in accordance with the magnitude of the potential difference. The TENS electrodes 38a and 38b are coupled to the secondary 142 of the TENS transformer 134 to provide for passage of an AC TENS current therebetween to facilitate the tissue healing process.

Figure 10:
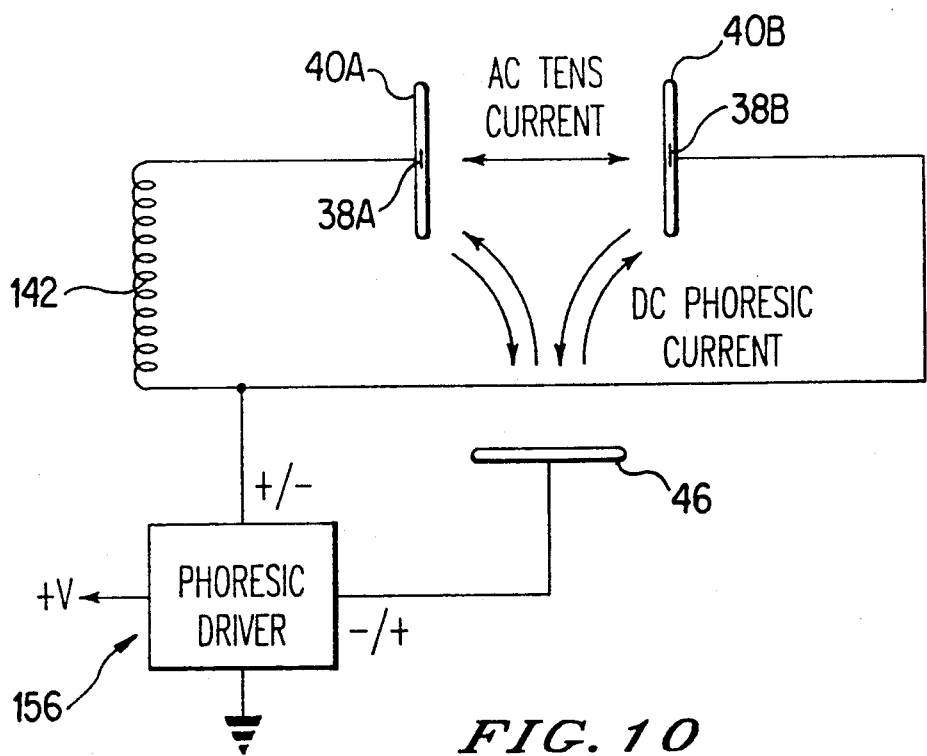
FIG. 10 is a schematic illustration of an alternative electrode configuration for use in the present invention.

In the three-electrode arrangement depicted in FIG. 10, the iontophoresis electrodes 40a and 40b are provided with the same polarity, and the third electrode 46 is provided with an opposite polarity. While this arrangement does not affect the AC TENS current which passes between the TENS electrodes 38a and 38b, it provides for the establishment of an electric field which extends between the electrodes 40a and 40b and 46. This field produces a phoresis current which can be adjusted in accordance with the relative position of the electrodes 40a, 40b and 46. This arrangement is particulary advantageous in instances where it is desirable to iontophoretically drive medicaments and other compounds into the skin in the immediate vicinity of the tissue treatment device 20, in which case the third electrode 46 can be positioned at a site optimally opposed from that of the electrodes 40a and 40b of like polarity. Alternatively, a plurality (i.e., two or more) of independently-operable electrodes can be provided for implementation of the phoresic field. Selection of appropriate combinations of electrodes can provide for a user-selectable directional field by which the device is operable to introduce an ionic compound into or along the tissue or skin of a patient.

Figure 11:
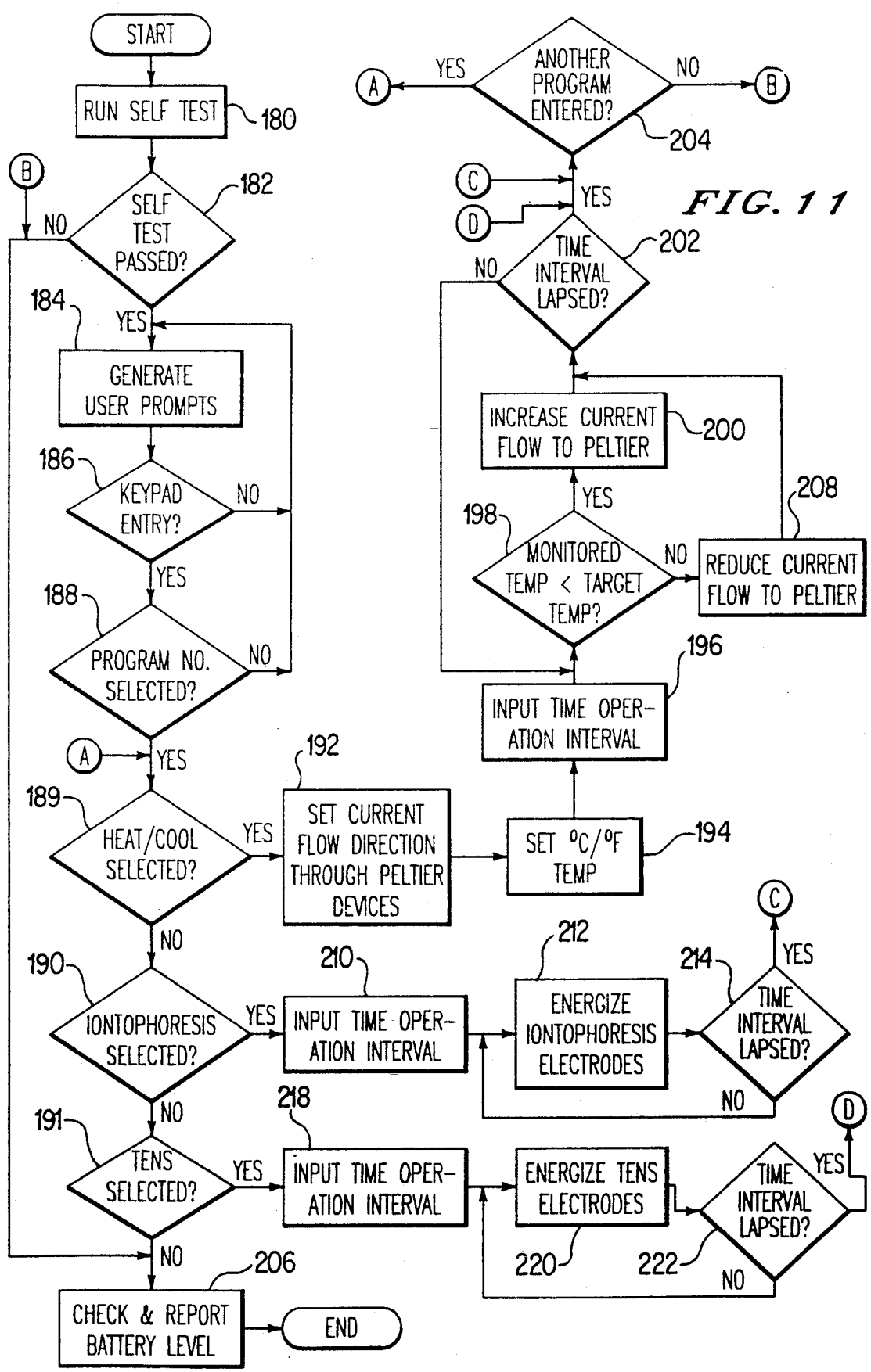
FIG. 11 illustrates a flow diagram for operating an apparatus in accordance with the teachings of the present invention.

Details of operation of the tissue treatment device 20 of the present invention and of the controller 24 thereof are illustrated in the flow chart of FIG. 11. With reference to the drawing, operational program software stored in RAM of the microprocessor unit 110 (FIG. 6-8) is operable upon system actuation to run a test of all of the system circuitry, as indicated by block 180. System actuation can be accomplished, for example, by switching the system from an "off" mode to an "on" mode in instances where a power switch is provided, or by actuation of one or more keys of the keypad 60. Upon completion of the test, as indicated by block 182, one or more user prompts are generated for display to the user at the controller display window 82. Such prompts could include, for example, instructions for sequential entry of commands for input of program number, selection of parameters (temperature, iontophoresis, TENS, and time), and the value of each parameter selected. Once the system has generated the appropriate prompts, a pause of prescribed duration is provided to allow the user to actuate one or more of the selector switches and keys of the keypad, as indicated by block 186. In instances where the predetermined time interval has elapsed prior to user input of a monitored key, the processor 110 is operable to again provide for the generation of user prompts, indicated at block 184. Upon actuation of the program number selector switch 76 (block 188), the microprocessor 110 is operable to receive appropriate signal inputs corresponding to the function selector switches 72, 74, 78 and 80, as indicated by decision blocks 189, 190 and 191. In instances where one of the heating and cooling selector switches 72 and 74 has been actuated, system program software is operable to command the microprocessor 110 to set the appropriate current flow direction through the Peltier devices 50, as indicated by block 192. Once the appropriate current flow direction has been effected, the software is operable to receive inputs corresponding to operation of the system in accordance with °C./°F., as indicated by block 194. Preferably, a default to an appropriate one of these two temperature systems is provided in instances were the user fails to depress the appropriate key 62 of the keypad 60. The default to °C./°F. is preferably in accordance with the measurement system in use where the device is to be operated. The time interval for system operation during the program is specified, as indicated by block 196. Time input can be accomplished, for example, upon actuation of the "time" selector switch 66 and entry of an appropriate combination of keys 62 which specifies the desired duration of system operation. The length of time entered into the system is preferably indicated in the display window 70 in a conventional fashion.

The operational software is preferably operable to monitor temperature on a continuous basis. In instances where the monitored temperature as detected by the temperature probe 59 is below the input target temperature, as indicated by block 198, appropriate signal input is produced by the microprocessor unit 110 to increase current flow to the Peltier thermoelectric devices, as indicated by block 200. A microprocessor unit clock (not shown) is operable throughout the program to provide signal inputs in accordance with the time remaining in the program. In instances where the preselected time interval has elapsed, as indicated by block 202, the operational software is operable to determine whether a further program has been entered into the system, as indicated by decision block 204. In instances where a further program has been entered, the program is recalled and run in the manner described above in connection with decision blocks 189, 190 and 191. In instances where no further program data has been entered, battery output is checked and reported, as is the case in instances where the outcome of the self-test indicated at block 182 is negative, as indicated by block 206. The battery level can be indicated in the display window 82 or by another means, such as by illumination of a battery replacement indicator light (not shown). Referring once again to decision block 198, in instances where the monitored temperature exceeds the preselected target temperature, the operational software commands the microprocessor to reduce current flow through the Peltier devices, as noted at block 208, and proceeds with time monitoring of the program in the manner discussed with reference to block 202.

In instances where neither heating nor cooling is selected (block 189), the programming software is operable to determine whether iontophoresis has been selected, as indicated by block 190. In instances where iontophoresis has been selected, the iontophoresis electrodes 40A, 40B and (optionally) 46 are energized for the time interval established in the program, as indicated by blocks 210 and 212. Elapsed time is preferably continuously monitored throughout running of the program, as indicated by decision block 214, resulting in continued energization of the iontophoresis electrodes until the predetermined time interval has elapsed. At that point, the program is operable to determine whether a further program has been entered in the manner noted above with respect to block 204.

A negative outcome of the iontophoresis selection in block 190 results in the TENS selection inquiry provided at block 191. A positive outcome of this inquiry results in the energization of the TENS electrodes 38A and 38B for the time interval specified, as indicated by blocks 218 and 220. As is the case with the foregoing two operation routines, elapsed time is preferably continuously monitored in a conventional manner, resulting in continued operation of the TENS electrodes until the preselected time interval has passed. Upon passage of the program interval, the program is operable to inquire in the manner described above as to whether a further program has been entered, as indicated at block 204. A negative outcome to the TENS selection inquiry indicated at block 191 results in implementation of the battery check and report indicated at block 206 and termination of the program.

It is to be appreciated from the foregoing detailed description that the tissue treatment device 20 of the subject invention can be configured and operated in a variety of different ways. For example, the treatment device can be configured so as to be applicable to specific portions of the body of an animal or human patient, and can be provided with one or a combination of the heating/cooling, iontophoresis, and transcutaneous electrical neurostimulation (TENS) functions internally or externally with respect to the body of a patient. The tissue treatment device can be further configured as a partially or completely disposable member, such as may be desirable in instances where the device is to be exposed to various bodily fluids of a patient. Furthermore, the various electrical circuit components can be incorporated into a separate controller in the manner described above, or, alternatively, can be mounted entirely or partially within the applicator device 22. In the latter case, the control input device 24 can be made detachable from the applicator device 22 so as to prevent any unauthorized tampering with the tissue therapeutic treatment program data. Tampering can also be prevented by modifying the operational program software stored in the microprocessor unit so as to be operable only upon receipt of an appropriate command code that is known only to authorized users of the equipment.

While the tissue treatment device of the subject invention has been described in connection with various preferred embodiments, it is to be understood and appreciated that departures therefrom are possible and are intended to be encompassed within the scope of the accompanying claims.

What is claimed is:

1. A temperature variable and iontophoretic device for application to the body of a patient, comprising:
   an outer support member;
   means coupled to said outer support member for selectively supplying thermal energy to the body of a patient or for removing thermal energy therefrom;
   means for selectively energizing said thermal energy supply and removal means for effecting thermal energy supply or removal form the body of the patient, said energizing means comprising a user-operable data input device; and
   means coupled to said outer support member for iontophoretically administering a compound to the body of the patient, wherein said data input device also selectively controls said iontophoretic administering means.

2. The device according to claim 1 wherein said thermal energy supply and removal means comprises a deformable member that is positionable against a portion of the body of a patient to assume the general shape of the body portion.

3. The device according to claim 2, wherein said deformable member comprises at least one sealed sac having a heat conductive fluid contained therein.

4. The device according to claim 1 or 2 wherein said support member comprises a flexible structure which is generally conformable to the portion of the patient's body over which the device is to be applied.

5. The device according to claim 1, wherein said thermal energy supply and removal means comprises at least one Peltier thermoelectric device.

6. The device according to claim 5, wherein said Peltier thermoelectric device is positioned between said outer support member and a deformable member positionable against a portion of the body of a patient to assume the general shape of the underlying body portion, said deformable member containing a heat conductive fluid.

7. The device according to claim 6, wherein said deformable member comprises an electric field responsive compound.

8. The device according to claim 6, wherein said data input means comprises programmable data processing means.

9. The device according to claim 8, further comprising means for monitoring the temperature of said fluid and feedback control means for controlling said Peltier thermoelectric device in accordance with any disparity between said monitored fluid temperature and a user-selected temperature value input into the processing means.

10. The device according to claim 9, wherein said processing means is operable to receive program input for at least two different user-selected temperature values and to control said Peltier device to effect a change in fluid temperature from one of sad user-selected temperature values to the other of said user-selected temperature values upon attainment of a user-selected parameter.

11. The device according to claim 10, wherein said user-selected parameter is time duration of treatment.

12. The device according to claim 10, wherein at least one of said user-selected temperature values and said user-selected parameter is input into said processing means by input means detachably coupled to said processing means.

13. The device according to claim 1, wherein said iontophoretic administering means comprises means for introducing the compound into the patient's body in a user-selectable direction relative to the surface of the patient's body to be iontophoretically treated.

14. The device according to claim 13, wherein said compound introducing means comprises first and second electrodes, at least one of said electrodes being selectively positionable along the patient's body so as to position the electrodes along a lie that is generally transverse to he surface to be iontophoretically treated.

15. The device according to claim 1, wherein said data input device comprises programmable data processing means.

16. The device according to claim 15, wherein said processing means is operable to receive a user-selected parameter and to terminate an electric field applied by said iontophoretic administering means upon attainment of said user-selected parameter.

17. The device according to claim 16, wherein said use-selected parameter is time duration of treatment.

18. The device according to claim 1, wherein at least a portion of the device is configured as a single use, disposable member.

19. The device according to claim 1, further comprising means coupled to said outer support member for implementing transcutaneous electrical neurostimulation.

20. The device according to claim 19, wherein said transcutaneous electrical neurostimulation implementing means is connected to said data input device, and wherein said data input device comprises a programmable data processing device.

21. The device according to claim 20, wherein said programmable data processing device receives as an input at least one of the following parameters:

elapsed time, electric field strength and voltage wave form.

22. The device according to claim 21, wherein said transcutaneous electrical neurostimulation implementing means and said iontophoresis administering means together comprise at lest two concentric electrodes.

23. A temperature variable device for applying transcutaneous electrical neurostimulation to the body of a patient, comprising:

an outer support member;

means coupled to said support member for applying transcutaneous electrical neurostimulation to the body of a patient;

means coupled to said support member for selectively supplying thermal energy to the body of a patient or for removing thermal energy therefrom; and means comprising a user-operable data input device for selectively energizing said thermal energy supply and removal means for effecting thermal energy supply or removal from the body of the patient, said energizing means comprising a user-operable data input device, said data input device also selectively controlling said transcutaneous electrical neurostimulation means.

24. The device according to claim 23, wherein said data input device comprises means for receiving an input corresponding to a user-selected input parameter.

25. The device according to claim 24, wherein said user-selected input parameter is time duration of transcutaneous electrical neurostimulation.

26. The device according to claim 23, wherein said user-operable data input device is detachably engageable with said outer support member.

* * * * *